United States Patent [19]

Guillet

[11] Patent Number: 4,525,255
[45] Date of Patent: Jun. 25, 1985

[54] PHOTOCHEMICAL REACTIONS FOR COMMERCIAL SYNTHESIS

[76] Inventor: James E. Guillet, 31 Sagebrush La., Don Mills, Ontario, Canada, M3A 1X4

[21] Appl. No.: 442,181

[22] Filed: Nov. 16, 1982

[51] Int. Cl.³ .............................................. B01J 19/12
[52] U.S. Cl. ......................... 204/158 R; 204/157.1 R; 204/159; 428/402
[58] Field of Search ............ 204/158 R, 159, 158 ST, 204/157.1 R, 157.1 W; 126/400; 428/67, 402

[56] References Cited

U.S. PATENT DOCUMENTS

| | | | |
|---|---|---|---|
| 3,994,675 | 11/1976 | Sasse et al. | 204/158 R |
| 4,045,315 | 8/1977 | Ryason | 204/157.1 W |
| 4,105,517 | 8/1978 | Ryason | 204/157.1 W |
| 4,298,439 | 11/1981 | Gafney | 204/158 R |
| 4,327,192 | 4/1982 | Henderson et al. | 428/402 |

FOREIGN PATENT DOCUMENTS 105625  8/1980  Japan ........................... 204/157.1 R Primary Examiner—Howard S. Williams

[57] ABSTRACT

Photochemical reactions are conducted using floating polymer beads on the surface of a moving body of water. The polymer bead is impregnated with a reactant, floated on the water in direct sunlight so as to expose the reactant to solar radiation, collected at a downstream location, treated to remove product from the polymer, and then the bead can be recycled. The process can be used to collect and store solar energy in chemical form, or for conducting photochemical synthesis to produce useful chemical products.

12 Claims, 7 Drawing Figures

PHOTOCHEMICAL REACTIONS FOR COMMERCIAL SYNTHESIS

FIELD OF THE INVENTION

This invention to photochemical reactions and more particularly to a process for conducting photochemical processes, using solar radiation, to produce useful chemical products.

BACKGROUND OF THE INVENTION

The utilization of solar radiation for producing useful chemical products and the production of useful energy has heretofore been hindered by economic considerations. The surface area of land which must be utilized to obtain useful amounts of solar energy, even in solar energy rich environments such as U.S. desert areas, is enormous using currently available solar energy collectors. All such solar collections need to be mounted and supported on land, in suitable disposition for solar energy collection. Even the mounting and supporting structures required to cover a sufficient land area to support enough conventional solar collectors to supply large amounts of power therefrom are prohibitively expensive.

A further difficulty with solar energy utilization arises from the fact that solar energy needs to be absorbed, and converted to a different energy form for utilization, the absorbing function and the converting function being best conducted at locations remote from one another for most efficient energy conversion. The solar energy absorption process should make most efficient use of the limited periods of maximum incidence of solar energy, i.e. exposure to direct sunlight. The conversion process can equally well be conducted continuously, independently of the presence or absence of direct incident sunlight, so that best overall efficiencies are accomplished by separately locating the absorbing and converting function. In this way, one function does not hinder or interfere with the other.

SUMMARY OF THE INVENTION

It is an object of the present invention to provide a novel solar energy utilization process.

It is a further object to provide a photochemical process for producing useful chemical products which is economically attractive.

In its broad aspect, the present invention provides a means for utilizing solar energy by causing incident solar radiation to effect photochemical reaction of a chemical reactant to produce a chemical product therefrom, while supported on a buoyant, inert carrier floating on water. The carrier material is in the form of discrete, small sized lumps or modules, e.g. beads, or buoyant foams which distribute themselves fully and evenly over the surface of a body of water, for maximum solar incident exposure. The reactant materials are carried and supported by the carrier materials in such a manner that they are not chemically affected by the carrier but are exposed to solar radiation while supported thereby, and the products formed by the photochemical reactions thereof are readily recoverable from the carrier material.

Thus according to the present invention, there is provided a process for producing chemical products by photochemical reaction of at least one photochemically reactive chemical reactant, which comprises:

supporting said at least one reactant on a water-buoyant inert carrier:

floating said carrier supporting said at least one reactant on a body of water;

exposing the carrier-supported reactant, while the carrier floats on the body of water, to solar radiation so as to cause photochemical reaction of said reactant to form a chemical product;

and recovering the chemical product so formed from the inert carrier.

DESCRIPTION OF THE PREFERRED EMBODIMENTS

In a preferred embodiment of the invention, the body of water is a moving body of water such as a natural or artificial lake, river, stream, reservoir etc. The carrier supporting the reactant is then conveyed, by the natural or induced water flow in the body of water, to a downstream product recovery location distanced from a reactant receiving location, with the solar energy absorption and photochemical conversion processes taking place during conveyance of the carrier therebetween. The chemical product so formed can be removed from the carrier following passage to the product recovery location, and then if desired the carrier can be recycled from the reactant receiving location.

Most suitably, the carrier material is a mass of buoyant beads or discs each comprising a substantially water-insoluble, UV-stable polymer. Thus the carrier may comprise hollow glass spheres coated with a suitable polymer, optionally covered with a protective film of low oxygen permeable polymer, or foam-cored plastic spheres provided with a suitable polymer coating. The water-insoluble, UV-stable polymer is treated, e.g. impregnated, with the reactant material so that it is swollen thereby, but does not chemically react with the reactant material. In similar manner, the product formed by photochemical reaction of the reactant while impregnated in the polymer, is similarly chemically inert to the chosen polymer and extractable therefrom, but nevertheless remains supported e.g. impregnated in the polymer until positive steps are taken to extract the product from the carrier. The type of polymer is thus chosen in conjunction with the reactants to be used and the products to be formed, with a view to arranging suitable inertness, support and product extractability.

In the alternative, the carrier can comprise a buoyant plastic or other foam material, capable of releasably holding and supporting the reactants and products and exposing them to solar radiation while floating on water.

The present invention can be put into practice in several ways. For example, it can be used for the production of useful organic chemical compounds by photochemical conversion of other organic compound reactants. It can also be used for the collection and storage of solar energy, by causing a reactant to convert photochemically to an energy-enriched product from which energy can be obtained in one form or another e.g. by reversing the chemical reaction in the absence of the solar radiation, or by some other energy-releasing utilization of the product (fuel, hydrogen-source etc.).

BRIEF REFERENCE TO THE DRAWINGS

The accompanying drawings illustrate aspects of embodiments of the present invention:

DESCRIPTION OF SPECIFIC PREFERRED EMBODIMENTS

Figure 1:
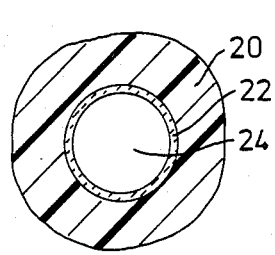
FIG. 1 is a cross-sectional view of a first embodiment of polymer-bearing bead useful in the invention.

FIG. 1 shows a cross-sectional view of one embodiment of the invention. The bead comprises a glass sphere 22 with a hollow interior 24. The sphere 22 is surrounded by a layer of cross-linked, swellable polymer 20, namely cross-linked polymethylacrylate.

The hollow sphere 22 acts as a buoyant particle surrounded by the swellable polymer layer 20 in which the photo chemically reactive reagents are retained and photochemically react on exposure to solar U.V. radiation.

Figure 2:
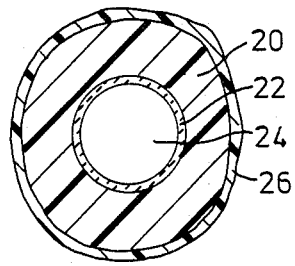
FIG. 2 is a cross-sectional view of an alternative form of polymer-bearing bead useful in the invention.

FIG. 2 illustrates a form of bead suitable for use where the photochemical reactions are inhibited by oxygen. It depicts a basically similar bead as shown in FIG. 1 with glass sphere 22 and hollow interior 24 surrounded by swollen polymer layer 20 in which the photochemically reactive reagent is contained, but also includes an outer thin film 26. Thin film 26 consists of a low oxygen permeably elastomer film that allows reactions to occur in the swollen polymer in the absence of oxygen, whilst permitting sufficient solar radiation to pass therethrough to reach polymer layer 20.

Figure 3:
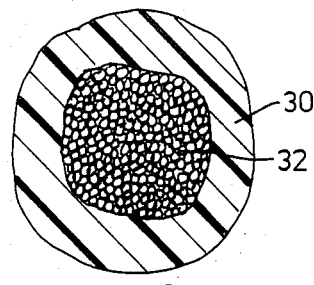
FIG. 3 is a cross-sectional view of a further form of polymer-bearing bead useful in the invention.

FIG. 3 shows another form of bead for use in the invention which consists of a spherically shaped bead with inner cross-linked expanded foam core 32 surrounded by a cross-linked polymer layer 30. The foam core 32 which contains air pockets and acts as a buoyant particle, similar to the hollow sphere in FIG. 1 described above, may be made of any polymer stable to solar U.V. radiation for example, polystyrene, polyacrylonitrile or polymethacrylonitrile and is most easily prepared by irradiation of prefoamed polymer beads. Cross-linking of the foam, which is caused by irradiation, must be sufficient to prevent destruction of the foam when exposed to swelling solvents.

Figure 4:
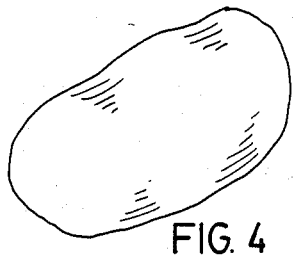
FIG. 4 is a top plan view of another form of polymer-bearing bead useful in the invention.
Figure 5:
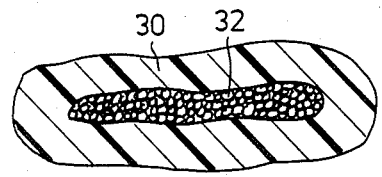
FIG. 5 is a cross-sectional view of the bead of FIG. 4.

A further useful form of bead, depicted in FIG. 4 and in FIG. 5, is of different shape but is similar in construction to that of FIG. 3. It has a flattened, disk-like shape, i.e. constituting a platelet. FIG. 5 shows the cross-linked foam core 32 which is surrounded by a thin layer 30 of cross-linked polymer. Both the core 32 and polymer layer 30 may be made of the same materials as those described in FIG. 3. The shape of this bead allows for a large area of exposure to solar radiation and thus efficient conversion of the reagents therein.

Figure 6:
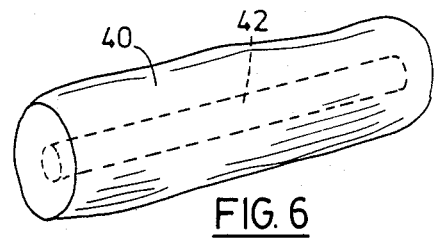
FIG. 6 is a perspective view of a different polymer-bearing bead useful in the invention.

FIG. 6 depicts another form of bead for use in the invention. The embodiment is a rod shaped bead with an inner core 42 surrounded by a thin polymer layer 40. The core may be made of any foamed or unfoamed low density polymer, for example polyethylene, and the polymer layer 40 may be made of any of a variety of polymers as described herein. Solid, buoyant polymer rods are also useful.

The dimensions of the beads as shown above, will depend on the thickness of the polymer layer which, in turn, depends on the extinction coefficient of reactive materials and their concentration in the polymer layer. Preferred layer thicknesses are in the range of 0.1 mm. to 2.0 mm., though greater layer thicknesses are also suitable.

The beads may be easily handled using any man-made or natural reservoir of water on which the beads will float, and fluidized bed techniques. They may be pumped readily as slurries in water or other solvents. The size of the beads is variable though preferably the beads should be of small size, suitably in the range of 0.2 to 5 mm. diameter.

The process of the invention contemplates the use of buoyant polymer beads, which float on the body of water. The density of the body of water can be increased, if desired, to promote the buoyancy of the beads, by dissolving salts in the water (sodium chloride, calcium chloride etc.). Such salted solar ponds are known. This provides a means by which normally non-water-buoyant polymer beads can be used as the carrier for photochemical reactions.

After the beads have been exposed to solar U.V. radiation for suitable length of time to convert the reagents contained therein photochemically, they are removed from the water, for example by filtration. Depending on the nature of the energy enriched or energy releasing product in the bead, the useful products are removed from the bead, for example by distillation or solvent extraction, and the beads are then recharged with fresh reagents, ready for re-use.

The exposure of the beads, and, consequently, of the reagents therein, may be controlled by controlling the rate of flow of surface water in the reservoir. Moreover, the beads will automatically spread themselves in a thin layer on the surface of the water, and, with sufficient wave action, uniform exposure of the beads occurs.

Figure 7:
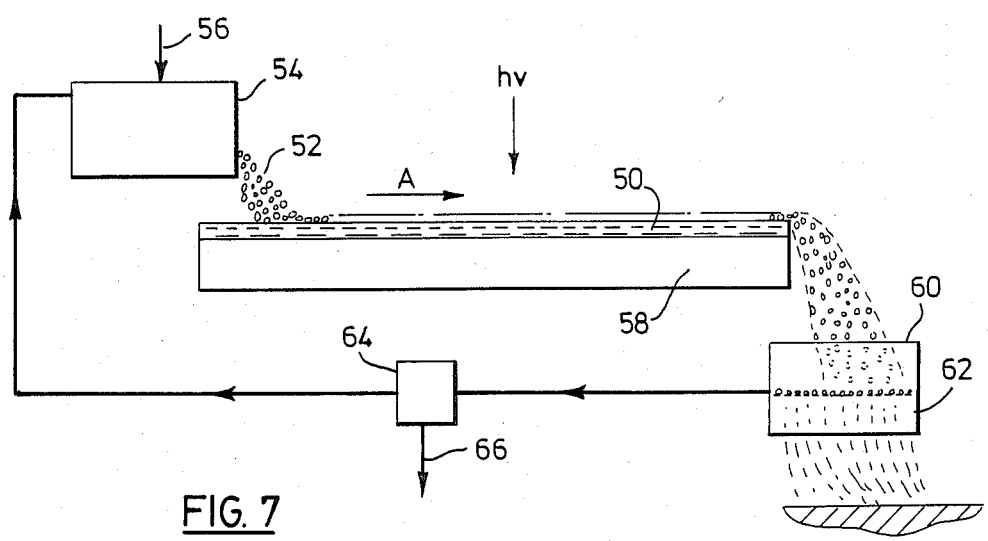
FIG. 7 is a diagrammatic illustration of the process of the present invention.

An embodiment of the process of the invention is illustrated schematically in FIG. 7. This shows a body of water 50 flowing in the direction of arrow A. Polymer-bearing, buoyant beads 52 of one of the types previously described, are fed to an impregnating vessel 54 disposed at an upstream location relative to the body of water for receiving chemical reactant. The reactant is fed to impregnating vessel 54 via inlet 56 and impregnates the beads therein. The impregnated beads are then poured onto the surface of the body of water 50, on which they float and spread out as a monolayer, thereby exposing the reactant impregnated therein to incident solar radiation as indicated. The beads 52 are transported by the moving body of water to a weir arrangement 58 over which the water and beads fall into a screened receiving vessel 60 where the beads, now impregnated with chemical reactant are separated from the water by screen 62 and fed to a product recovery vessel 64, where the chemical product is separated from the beads, e.g. by solvent extraction, and recovered via exit 66. The beads 52 are then recycled via line 68 for re-impregnation in vessel 54 with reactant and repeat of the cycle.

The polymer for use as the carrier for the reactants and products can be chosen from a wide variety of different polymers, having regard to the function which it is to perform. The polymer must be chosen with regard to its ability to retain the specific reactants and products in a stable but readily recoverable manner, and without chemically reacting or interfering witn the reactants, products or course of reaction therein. Organic polymers and organic compounds generally show a reasonable degree of compatibility with one another, with the compounds having a solubility in the polymers, to various extents. The polymer must be stable on exposure to UV and other solar radiations. It must be substantially unaffected by water—where normally water soluble polymers are to be used, they are used in cross-linked form to import the necessary water resistance. Preferred polymers are capable of repeated cycles of impregnation with reactant, floatation and product removal, so that the beads used in the invention are re-usable many times over. Useful polymers can be chosen from among the following:

cross-linked polymetnylacrylate;
cross-linked polyethylacrylate;
cross-linked ethylene-vinyl acetate copolymers;
cross-linked polyvinyl acetate;
cross-linked polyvinyl alcohol;
cross-linked polymers and copolymers of hydroxyethyl acrylate;
cross-linked polymers and copolymers of hydroxyethyl methacrylate;
cross-linked polymers and copolymers of hydroxyethyl ethacrylate;
cross-linked acrylamide polymers and copolymers;
cross-linked N-substituted acrylamide polymers and copolymers;
cross-linked polymers and copolymers of acrylonitrile polymethacrylonitrile;
cross-linked ethylene-ethyl acrylate copolymers;
cross-linked etnylene-acrylic acid copolymers;
cross-linked ethylene-methacrylic acid copolymers; polystyrene;
poly (alphamethylstyrene)
semi-crystalline polyethylene (optionally cross-linked);
semi-crystalline polypropylene (optionally cross-linked);
ethylene-propylene copolymers and terpolymers;
cross-linked silicone polymers;
fluorocarbon polymers e.g. polyvinyl fluoride and polyvinylidene fluoride;
polyvinylchloride (suitably stabilized to import the necessary degree of UV resistance) polyamides;
polyesters;
poly (amide-imides)
polyaminoacids, semicrystalline or cross-linked proteins;
cellulose and its derivatives;
polyurethanes;
polyepoxides;
cross-linked polyethylene oxide;
cross-linked polypropylene oxide;
polyisobutylene;
polyisoprene;
polybutadiene;
SBR copolymers;
chlorosulfonated rubbers;
rubber hydrochloride;
hydrogenated rubber; cross-linked hydrogels.

Cross-linked polymers have the additional advantage that they swell to a high degree to provide for ready impregnation with reagents and removal of products.

Preferred polymers for use in the invention have a glass transition temperature below that at which the impregnation and extraction takes place. If the polymer is in its glassy state, i.e. below its glass transition temperature, the diffusion of the chemical into the polymer is hindered, so that impregnation is slowed. Above this temperature, the mobility of the chemical reactants and products is enhanced, leading to shorter impregnation, recovery and reaction times, especially where a bimolecular reaction is to be accomplished.

Specific preferred polymers are cross-linked ethylene-vinyl acetate copolymers and cross-linked ethylene-acrylic acid copolymers.

In one of its aspects, the present invention can be utilized as a means of photosynthesis of organic chemicals. There are a number of useful organic chemical compounds whose only or whose most efficient synthesis involves a photochemically induced reaction. The present invention provides a simple and efficient means by which such reactions can be conducted using natural solar radiation and hence avoiding the conventional artificial lamp uses and exposures. In providing pharmaceutical products for example, especially those requiring a chemical ring-forming or ring-opening reaction, photochemical synthesis is often the preferred method.

A specific example of organic chemical synthesis which can be conductd by the process of the present invention is formaldehyde synthesis from carbon monoxide in the presence of water and metal complexes:

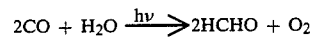
$$2CO + H_2O \xrightarrow{h\nu} 2HCHO + O_2$$

Polymer beads are impregnated with carbon monoxide and an appropriate organic soluble metal complex, e.g. ferric carbonyl, floated on a body of water in exposure to direct sunlight, and formaldehyde and the metal complex catalyst subsequently recovered from the bead. The formaldehyde so formed is useful in a variety of purposes, including conversion to methanol for use as a fuel. This reaction to produce formaldehyde is similar to natural photosynthesis. The choice of polymer in the bead for this reaction is made on the basis of criteria previously discussed—inertness to water, reactants and products, ability to hold but also to release readily the reactants and products and the catalyst or photosensitizer necessary for the reaction, radiation transparency or translucency etc.

An alternative manner in which the process of the invention may be conducted, in using a gaseous reagent such as carbon monoxide, or in adopting a chemical reaction or compound which is sensitive to oxygen, is to cover the floating beads on the water surface with a solar radiation permeable membrane, under which is provided an atmosphere of reactant or inert gas. The membrane may be supported by the atmosphere of gas beneath it, to exclude oxygen from the vicinity of the impregnated floating beads or provide for their contact with a reactant gas.

The following are additional examples of organic chemical conversions which can be effected using the process of the present invention. Many of these can be used as energy storage and conversion means, as noted.

(a) Cis-trans Interconversion of Stilbene

At the appropriate wavelength or U.V. radiation the trans-isomer of stilbene will absorb energy and convert completely to the less stable cis-isomer:

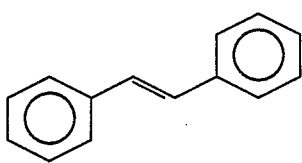

trans-stilbene

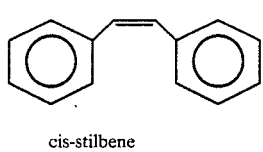

cis-stilbene

Reconversion of the cis-isomer back to the trans-isomer will release energy, as heat, that may be harnessed and utilized.

(b) Reduction of Quinones

Quinones undergo reversible oxidation-reduction reactions on exposure to solar radiation:

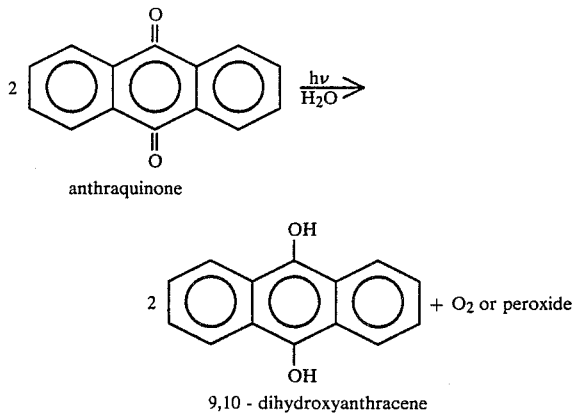

Reduction by solar U.V. radiation exposure, of anthraquinone in the polymer layer during the process of this invention, to 9, 10 -dihydroxyanthracene, involves the absorption of a specific quantity of energy, known as the reduction potential. The 9, 10 - dihydroxyanthracene may then be removed from the polymer bead and subsequent oxidation will yield anthraquinone and energy.

(c) Oxidation of an Internally-unsaturated Olefin

For example, squalene can be photochemically oxidised, in the presence of oxygen and sunlight, to form a hydroperoxide derivative thereof which is useful in a number of chemical reactions.

(d) Photochemical Disproportionation of Ketones

For example, ketones of hydrocarbons in which the ketonic group is located at a non-terminal carbon atom of the hydrocarbon cnain will disproportionate on exposure to sunlight, to form smaller ketones and hydrocarbons by chain scission (Norrish reactions).

(e) Addition of Singlet Oxygen to Various Compounds Using Bound Sensitizers

An example of such a photochemical process is the production of the fragrance "Rose Oxide", by photooxygenation of citronellol with rose bengal as sensitizer. Isomeric hydroperoxides are produced, which can be reduced to alcohols, rearranged and cyclized to rose oxide.

(f) Photosynthesis of Vitamin D

7-Dehydrocholesterol (obtainable by known processes from cholesterol, a natural product readily available from, e.g. cod liver oil) undergoes a photochemical ring opening process on UV irradiation to give previtamin D3, which on warming readily gives the thermodynamically more stable vitamin $D_3$

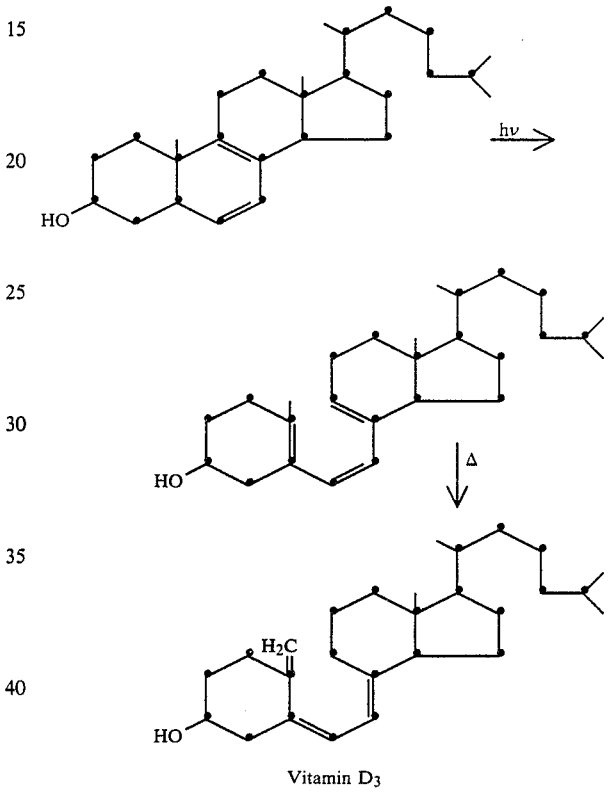

Vitamin $D_3$

The only commercial method of synthesis of vitamin D is photochemical, the current energy costs for which are substantial. Such a photochemical process is advantageously conducted according to the present invention, since the steroid reactants and products are relatively high molecular weight and hence non-volatile on exposure to sunlight. They are suitably impregnated into and removed from an ethylene-vinyl acetate copolymer as carrier.

Other photochemical synthesis of pharmaceutically useful steroids such as the production of hydroxy derivatives of vitamin $D_3$ and the production of dydrogesterone (a sex hormone) from a pregnadiene derivative, are also advantageously used in the present invention.

(g) Photoisomerization of Vitamin A Acetate

The industrial process for producing vitamin A acetate (Wittig synthesis) produces a mixture of stereo-isomers, only one of which, the all-trans isomer is useful. The 11-cis form in the mixture can be photochemically converted to the all-trans form by the process of the present invention.

Sensitizers used to promote photochemical reaction in the process of the present invention are compounds capable of absorbing solar radiation and transferring it to the reactants, either radiatively or non-radiatively. The appropriate sensitizers may be chemically bound to the polymer layer or to the reactant, but removable from the product after the reaction is complete. They can if desired be left bonded to the polymer beads, if the beads are to be re-used in the same or similar reactions. They can be bound to the polymer in a similar way to that of UV stabilizers commonly used with polymers, or used in other ways analogously to known polymer stabilizer uses.

The types of products which can be synthesized according to the invention, and the reactants which can be used, should have a relatively low vapour pressure in order to be retained in the polymer films for the required exposure times (anywhere from a few hours to, say, one month, depending upon the thickness of the layer and other factors). Where the reactants and/or products are normally unacceptably volatile, they can be introduced into the polymer bead as a complex, which can be made to give up the product/reagent on demand, chemically or thermally. The products and reactants should also be relatively stable to oxygen if they are to be exposed on open bodies of water. Use of beads of the type shown in FIG. 2 can be used in instances of high oxygen sensitivity.

In another of its aspects, the present invention can be utilized as a solar energy collection and conversion means. As noted above, it can be used to conduct reversible chemical reactions which when reversed, yield useful energy. In addition, however, the present invention can be used to provide fuels for fuel cell utilization, and to generate and store hydrogen fuel.

As an example of such an aspect of the invention, the quinone-hydroquinone redox reaction may be considered. Under solar radiation and in the presence of water, benzoquinone is reduced to hydroquinone:

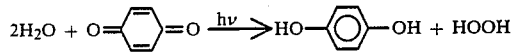

Hydrogen can be obtained by subjecting an aqueous solution of the reduced, hydroquinone compound to electric current, whereupon hydrogen is generated and the oxidised form benzoquinone is re-formed. The electrical power required to produce a standard amount of hydrogen from such a hydroquinone solution is approximately half that required to produce the standard amount of hydrogen by the normal process, electrolysis of water. Accordingly, the process of the present invention provides a means for obtaining hydrogen fuel using solar energy. The reduced product can either be fed to a fuel cell and oxidized therein to obtain electrical energy, or treated to release hydrogen, in an economically efficient manner.

This process can also be viewed as a process for storing hydrogen, in a chemically combined form. The generation of hydrogen gas in large quantities, ready for use as a fuel, poses serious storage problems, necessitating the use of pressurized, heavy storage tanks and cylinders. The storage of the hydrogen in chemically combined but readily available form, e.g. as a hydroquinone, reduces such problems.

It will be understood that the quinone-hydroquinone reversible redox reaction discussed above is merely a representative example of a redox reaction which can be used for this purpose in the process of the present invention. The system can be generalized, as follows:

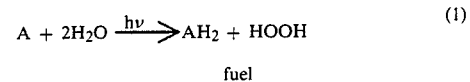

Reaction (1) takes place in the floating polymer beads, according to the invention, as previously described. A represents any organic compound capable of being photo-reduced in water. It is effectively acting as a chemical "carrier" of hydrogen, for generation and utilization of hydrogen. There are now two alternative reverse reactions to choose:

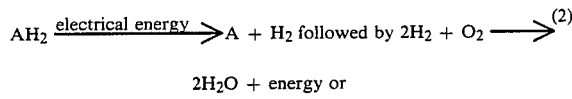

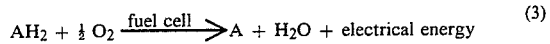

Reaction (2) produces hydrogen fuel which is subsequently used in energy production.

Reaction (3) produces electrical energy directly through fuel cell utilization. In either case compound A is regenerated, ready for recycling.

Additional examples of reversible redox couples which can be photochemically reduced in the presence of water, and can hence be used in the process of the present invention, are adenosine triphosphate⇌adenosine diphosphate, and the aforementioned anthraquinone⇌9,10-dihydroxyanthracene.

A still further aspect of the present invention concerns nitrogen fixation. The plastic bead or foam system used in the present invention can be used to retain photocatalysts suitable for the fixation of nitrogen from the atmosphere using natural sunlight as the source of energy, to form nitrogenous compounds useful as fertilizers. Such catalysts are normally transition metal catalysts. The nitrogenous compounds are formed in the polymer of the bead itself, and can be recovered therefrom. Alternatively, the beads may be made of a biodegradable polymer, so that the combined beads and nitrogenous product can be utilized as fertilizer.

The economic features of the process of the present invention are highly attractive, in comparison with the capital and energy costs of conventional, silicon-based solar energy collectors and associated convertors. At the current state of the art, silicon solar cells cost about $100 per square meter of radiation-incident surface, not counting installation, transformer and transmission costs. A one-hectare installation thus costs $1,000,000. The actual costs of electricity produced from such devices are estimated to exceed 20–50 c per kilowatt-hour. In the present invention, 1 kg of polymer will cover 1 square meter of pond surface to a thickness of 1 mm, which at 50 c per pound of polymer calculates to a capital cost of about $10,000 to cover one hectare of water surface. Even at low energy conversion efficiencies, potential economic advantages of the present invention are significant.

The following specific examples illustrate the process of the invention.

EXAMPLE 1

Crosslinked ethylene-vinylacetate copolymer beads were prepared by the following procedure. Ethylene-vinylacetate beads (500 g, ELVAX 150) containing approximately 33% vinylacetate were placed in a sealed vessel, evacuated and flushed with nitrogen. They were irradiated for three weeks with γ-rays from a cobalt-60 source. The total dose required for crosslinking was about 15 megarad. After γ-irradiation the beads were placed in a Soxhlet extractor and extracted with toluene until no further soluble materials could be recovered. The beads were then dried under vacuum at 40° C. and stored for future use.

EXAMPLE 2

Crosslinked ethylene-vinylacetate beads (10 g) were placed in a test tube along with 5 cc of a 2% solution of 2-undecanone in pentane. The test tube was stoppered and placed in a water bath at 35° C. After one hour all of the solvent had been absorbed by the beads. The beads were then dried in air and exposed to outdoor sunlight by floating them on a developing tray containing water. After two days of exposure to outdoor sunlight, 15% of the 2-undecanone had been converted to octene.

EXAMPLE 3

Crosslinked ethylene-vinylacetate beads (20 g) were placed in a flask and gently agitated while 5 cc of a 2% solution of decanophenone was added. After agitating at room temperature for 30 min. all of the solution was absorbed by the beads. The beads were removed, dried and exposed for three days floating on the surface of water in a flat dish. After exposure, the beads were placed in a container with 20 cc of toluene. After standing for three hours, the excess toluene was decanted and additional 20 cc was added. This procedure was repeated until no further product could be removed from the beads. The toluene extracts were then analyzed by gas chromatography. The results indicated that substantially all of the starting material had been converted to photoproducts of which the major product was acetopnenone.

EXAMPLE 4

Crosslinked ethylene-vinylacetate beads (38 g) were immersed in 100 ml of squalene sensitized with 5 mg of rose bengal dye. After 48 hr the beads were removed and dried. Approximately 3.5 g of squalene had been taken up by the beads. The beads were floated over distilled water in a tray covered with a thin polyethylene film and were exposed to radiation from a sunlamp for six hours, after which they were removed from the surface of the water and extracted eight times with absolute methanol. The amount of hydroperoxide was determined by the change in absorbance at 260 nm when treated with triphenylphosphene. Based on the peroxide analysis, 6.4% of the double bonds of the squalene had been converted to the corresponding hydroperoxide. This procedure was repeated, except that the samples were exposed to ultraviolet light on the roof of a building for three days. Based on UV analysis the conversion to hydroperoxide was 3%.

EXAMPLE 5

7-Dehydrocholesterol (0.046 g) were dissolved in 4 ml of anhydrous ether. Crosslinked ethylene-vinylacetate beads (1 g) were added to the solution. After one hour all of the solution was absorbed by the beads. The beads were air dried. The concentration of 7-dehydrocholesterol remaining in the beads was approximately 5 wt-%. The beads were then floated on water in a tray and irradiated for a total of 48 hours in natural sunlight. The weather was cloudy during this period and very little direct sunlight reached the beads. After exposure, the beads were extracted with ether and analyzed by obtaining the UV spectra. Based on the UV analysis, approximately 60% of the 7-dehydrocholesterol had been converted to the previtamin D. Heating the ether solution of the previtamin at 60° C. for two hours converted the previtamin to vitamin D.

EXAMPLE 6

Low density polyethylene beads approximately 2 mm in diameter (Tenite 800E) were extracted with 95% ethanol in a Sohxlet extractor and dried. This polymer is non-crosslinked, and has limited crystalline regions. 50 g of the beads were placed in a flask with 20 ml 2-undecanone and heated to 60° C. overnight. The amount of 2-undecanone absorbed was determined by extraction of a small sample (2 g) with ethanol followed by G.C. analysis. Samples of the beads were floated on water in a photographic tray and exposed for (1) 28 hrs, and (2) 60 hrs to natural sunlight. A further sample (sample 3) was exposed to a sunlamp for 16 hrs.

The exposed beads were collected, rinsed with water to remove surface dust and dirt, then extracted 6–8 hrs with ethanol. The extracts were analysed by G.C. The conversion to octene and acetone was 18% for sample 1, 40% for sample 2 and 35% for sample 3. The yield of acetone was lower than expected because of the loss of this volatile compound from the beads.

I claim:

1. A process for converting at least one photochemically reactive chemical reactant to photochemical reactions products by exposure to solar radiation, which comprises:
   providing a carrier which is buoyant on an aqueous liquid medium, and substantially inert to the chemical reactant and the photochemical reaction products;
   applying said at least one reactant to the carrier and supporting it thereon or therein;
   floating said carrier supporting said at least one reactant on an aqueous medium in which the carrier is substantially insoluble and inert;
   causing photochemical reaction of or between said photochemically reactive chemical reactant or reactants, without the involvement of the supporting aqueous medium therein, by exposing the carrier-supported reactant or reactants to solar radiation while the carrier floats on the aqueous liquid medium;
   and recovering from the inert carrier photochemical reaction products obtained from said reactant or reactants.

2. A composition for use in the photochemical production of useful energy enriched and energy releasing products comprising:
   a non-water soluble, swellable water buoyant polymer bead, said bead comprising a polymer layer surrounding a buoyant particle of density less than that of water, said polymeric layer being swollen with at least one non-water soluble chemical reagent capable of undergoing a photochemical reaction on exposure to solar radiation.

3. A processs of converting at least one photochemically reactive chemical reactant to a photochemical reaction product thereof by exposure to photoradiation which comprises:

exposing said reactant to solar radiation while supported on an inert, water insoluble, buoyant polymer carrier in the form of discrete modules floatint on a moving body of water, for a sufficient time to effect the desired photochemical conversion.

transporting said carrier modules on the moving body of water during solar radiation exposure from a first, reactant receiving location to a second, product recovery location;

subsequently recovering the polymer carrier from the moving body of water;

and subsequently extracting photochemical reaction product from said polymer carrier.

4. A processs for converting at least one photochemically reactive chemical reactant to photochemical reaction products by exposure to solar radiation, which comprisies:

providing a carrier which buoyant on an aqueous liquid medium and substantially inert to the chemical reactant and the photochemical reaction products;

applying said at least one reactant to the carrier and supporting it thereon or therein;

distributing the carrier supporting said at least one reactant over the surface of a body of water in which the carrier is substantially insoluble and inert;

exposing the carrier-supported reactant, whilst the carrier floats on the body of water, to direct solar radiation so as to cause photochemical reaction of said reactant to form a product;

transporting the carrier on the surface of the body of water from a first, reactant receiving location to a second, product recovery location, during said solar radiation exposure;

and recovering the product so formed from the inert carrier.

5. The process of claim 4 wherein said inert carrier is a water buoyant bead comprising a substantially water insoluble, UV-stable polymer, said reactant being supported on the carrier by impregnating the polymer with the reactant.

6. The process of claim 5 wherein the photochemical reaction of reactant to chemical product is reversible to release energy in re-formation of the reactant.

7. The process of claim 6 wherein the reverse, energy releasing reaction is carried out following recovery of the chemical product from the inert carrier.

8. The process of claim 7 wherein the reactant reformed in the reverse reaction is recycled through the process by re-impregnation in the polymer of the carrier followed by water flotation and solar radiation exposure thereof.

9. The process of claim 6 wherein the reactant is an organic compound capable of reduction in the presence of water and solar radiation, to form a product which is capable of oxidation to release hydrogen and re-form the reactant.

10. The process of claim 9 wherein the reactant is quinone and the product is hydroquinone.

11. The process of claim 5 wherein the reactant is 7-dehydrocholesterol and the product is previtamin $D_3$.

12. The process of claim 5 wherein the polymer has a glass transition temperature below the temperature of application of the reactant thereto.

* * * * *